United States Patent
Fleute-Schlachter et al.

(10) Patent No.: US 8,901,165 B2
(45) Date of Patent: Dec. 2, 2014

(54) ALKOXYLATED GLYCEROL ACETALS AND THEIR DERIVATIVES

(75) Inventors: Ingo Fleute-Schlachter, Essen (DE); Sandra Mack, Korschenbroich (DE); Peter Kempers, Mönchengladbach (DE); Ulrich Schörken, Düsseldorf (DE); Eckhard Paetzold, Broderstorf Pastow (DE); Udo Kragl, Kritzmow (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 13/499,324

(22) PCT Filed: Sep. 23, 2010

(86) PCT No.: PCT/EP2010/005825
§ 371 (c)(1),
(2), (4) Date: Mar. 30, 2012

(87) PCT Pub. No.: WO2011/038857
PCT Pub. Date: Apr. 7, 2011

(65) Prior Publication Data
US 2012/0184443 A1    Jul. 19, 2012

(30) Foreign Application Priority Data
Oct. 2, 2009    (EP) .................................... 09012496

(51) Int. Cl.
A01N 43/28    (2006.01)
A01N 43/32    (2006.01)
C07D 319/06   (2006.01)
C07D 317/18   (2006.01)

(52) U.S. Cl.
CPC ............ *C07D 317/18* (2013.01); *C07D 319/06* (2013.01); *A01N 43/28* (2013.01); *A01N 43/32* (2013.01)
USPC ............ 514/452; 514/467; 549/372; 549/543

(58) Field of Classification Search
USPC ....................................... 549/372
See application file for complete search history.

(56) References Cited

U.S. PATENT DOCUMENTS

| 4,031,112 A * | 6/1977 | Oppenlaender et al. ...... 549/333 |
| 2008/0293602 A1 | 11/2008 | Kodali et al. |
| 2008/0312085 A1 * | 12/2008 | Kordes et al. .................. 504/247 |
| 2010/0069509 A1 * | 3/2010 | Steinbrenner et al. ........ 514/772 |

FOREIGN PATENT DOCUMENTS

| EP | 0742177 | 11/1996 |
| GB | 2020702 | 11/1979 |
| GB | 2020702 A * | 11/1979 .............. D06P 1/16 |

OTHER PUBLICATIONS

"International Search Report of WO2011/038857", mailed on Jul. 12, 2011, 6 pages.
Nikitina, L. P. et al., "Vinyl Ethers Containing an Epoxy Group: XXI. Synthesis and Acid-Catalyzed Cyclization of 1-[omega-(Vinyloxy)alkoxy]-3-(2-propynyloxy)-2-propynols—A Simple route to 2-Propynyloxymethyl-Substituted Cyclic Polyethers", *Russian Journal of Organic Chemistry*, vol. 39, No. 10 2003, pp. 1384-1392.
Wirth, W. et al., "Mechanisms Controlling Leaf Retention of Agricultural Spray Solutions", *Pestic. Sci.*, vol. 33 1991, pp. 411-420.

* cited by examiner

*Primary Examiner* — Golam M M Shameem
*Assistant Examiner* — Laura Daniel
(74) *Attorney, Agent, or Firm* — Servilla Whitney LLC

(57) ABSTRACT

Described are alkoxylated glycerol acetals according to Formulas (Ia) and (Ib)

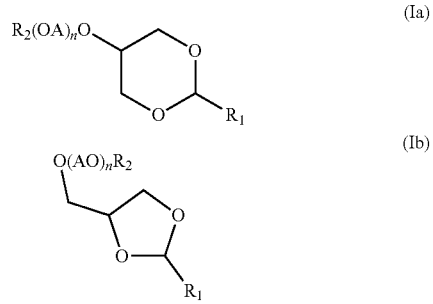

wherein $R^1$ represents a linear or branched, saturated or unsaturated and optionally substituted hydrocarbyl residue comprising 6 to 22 carbon atoms and 0 or 1 to 3 double bonds, a benzyl or furfuryl radical, $R^2$ is selected from hydrogen, an alkyl, alkenyl or hydroxyalkyl group having 6 to 22 carbon atoms or an acyl group having 6 to 22 carbon atoms and 0 or 1 to 3 double bonds, AO represents an ethylene oxide, a propylene oxide, a butylene oxide unit, or their mixtures, and n is an integer of about 1 to about 100.

6 Claims, No Drawings

ALKOXYLATED GLYCEROL ACETALS AND THEIR DERIVATIVES

CROSS-REFERENCE TO RELATED APPLICATIONS

This application is the National Stage entry of PCT/EP2010/005825, filed on Sep. 23, 2010, which claims priority to European Patent application number 09012496.7, filed on Oct. 2, 2009, both of which are incorporated herein by reference in their entireties.

TECHNICAL FIELD

The present invention is related to the area of agrochemicals and refers to new low-foaming surface-active agents with improved surface tension reduction, two processes for obtaining them and their use as additives for agrochemical compositions, lacquers and paints.

BACKGROUND

It is known that an inverse correlation between dynamic surface tension and leaf retention of agricultural spray solutions exists i.e. the lower the surface tension the better the leaf penetration (see e.g. W. Wirth, S. Storp & W. Jacobsen in Pestic. Sci. 1991, 33, 411-420: *Mechanisms Controlling Leaf Retention of Agricultural Spray Solutions*).

In the market, many different surface-active agents for enhancing leaf penetration by improved wetting power can be found. Usually, fatty alcohols are used as starting materials which are then converted into high alkoxylates, belonging to the class of non-ionic surfactants. Unfortunately, said surfactants show different disadvantages: While reduction of dynamic surface tension in aqueous solutions is mediocre, they reduce significantly static surface tension, but too much foam is generated in the final application. To reduce foam, branched alcohols such as isotridecanol or 3,5,5 trimethylhexanol can be used as starting materials for higher alkoxylates. Yet, such starting alcohols are not even partially based on renewable resource. Hence, they are often objected for lacking a sufficient degree of biodegradability.

Therefore, the problem underlying the present invention has been to develop new additives for agrochemical compositions, lacquers and paints based on environmental friendly renewable resources, showing

- dynamic surface tension at a bubble frequency of 10 Hz at aqueous concentrations of 0.25% or lower, a maximum of 50 mN/m;
- quasi-static surface tension at a bubble frequency of 0.1 Hz at aqueous concentrations of 0.25% or lower, a maximum of 40 mN/m; and
- foam generation at 0.1% b.w. aqueous concentration a maximum of 150 ml (determined using a SITA foam tester R-2000).

SUMMARY

Embodiments of the present invention are directed toward alkoxylated glycerol acetals according to Formulas (Ia) and (Ib), wherein $R^1$ represents a linear or branched, saturated or unsaturated and optionally substituted hydrocarbyl residue comprising 6 to 22 carbon atoms and 0 or 1 to 3 double bonds, a benzyl or furfuryl radical, $R^2$ is selected from hydrogen, an alkyl, alkenyl or hydroxyalkyl group having 2 to 22 carbon atoms or an acy group having 2 to 22 carbon atoms and 0 or 1 to 3 double bonds, AO represents a mixture of ethylene oxide and propylene oxide units, and n is an integer of about 1 to about 100.

In one or more embodiments, $R^1$ represents a linear or branched alkyl radical having 8 to 12 carbon atoms.

In one or more embodiments, $R^2$ is selected from hydrogen, an alkyl radical having 4 to 8 carbon atoms, or an acyl radical having 4 to 8 carbon atoms.

In one or more embodiments, AO represents mixtures of ethylene and propylene units, either randomized or blockwise.

In one or more embodiments, n is an integer of about 4 to about 20.

Other embodiments of the present invention are directed to an alkoxylated glycerol acetal comprising n-octyl glycerol acetal+4PO+4EO, and to an alkoxylated glycerol acetal comprising n-decyl glycerol acetal+4PO+4EO.

Further embodiments of the present invention are directed to an alkoxylated glycerol acetal comprising iso-nonyl glycerol acetal+3PO+3EO, and to an alkoxylated glycerol acetal comprising iso-nonyl glycerol acetal+3EO+PO.

A still further embodiment of the present invention is directed to an agrochemical composition comprising a biocide, and an alkoxylated glycerol acetal according to general Formulas (1a) and (1b).

DETAILED DESCRIPTION

The present invention provides for alkoxylated glycerol acetals according to Formulas (Ia) and (Ib)

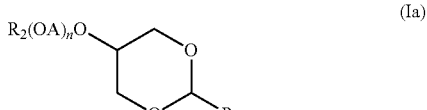

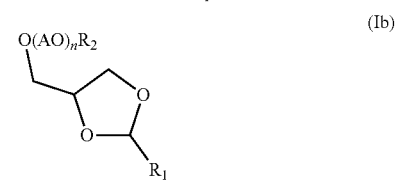

wherein $R^1$ represents a linear or branched, saturated or unsaturated and optionally substituted hydrocarbyl residue comprising 6 to 22 carbon atoms and 0 or 1 to 3 double bonds, a benzyl or furfuryl radical, $R^2$ is selected from hydrogen, an alkyl, alkenyl or hydroxyalkyl group having 2 to 22 carbon atoms or an acyl group having 2 to 22 carbon atoms and 0 or 1 to 3 double bonds, AO represents an ethylene oxide, an propylene oxide, an butylene oxide unit or their mixtures, and n stands for an integer of about 1 to about 100.

Quasi-Static or equilibrium surface tension at an air-liquid interface can be determined by the Du Noüy ring method, the Wilhelmy plate or the like. When it comes to measuring polymers, by-products with low molecular weight can create agglomerates at the surface and lead to artifacts suggesting very low surface tensions. To avoid such problems, a dynamic method is used but the frequency is reduced to 0.1 Hz or less, thus close enough to equilibrium conditions. Surprisingly, it has been observed that alkoxylated glycerol acetals and their derivatives are low foaming and show a serious reduction in surface tension, both under dynamic and quasi-static conditions. The products therefore fulfill the complex profile as explained above perfectly.

Alkoxylated Glycerol Acetals

Acetalisation of glycerol represents a well known process in organic chemistry and usually leads to a mixture of 1,2 and 1,3 cyclic acetals. In one or more embodiments, the alkoxylated glycerol acetals show a particular low foam generation and a capability to lower surface tension significantly and follow general Formulas (Ia) and (Ib) in which $R^1$ stands for an linear or branched alkyl radical having 8 to 12, more preferably 8 to 10 carbon atoms, a benzyl or furfuryl radical and/or $R^2$ stands for hydrogen, an alkyl radical having 4 to 8 carbon atoms or an acyl radical having 4 to 8 carbon atoms.

With respect to the polyalkylene glycol chain, in one or more embodiments AO stands for mixtures of ethylene and propylene units, either randomised or blockwise. Particularly good results are obtained using species where n is an integer of about 2 to about 50, preferably about 4 to about 20. In one or more embodiments, examples of alkoxylated glycerol acetals encompass—but are not limited to—n-octyl glycerol acetal+4PO+4EO, n-decyl glycerol acetal+4PO+4EO, iso-nonyl glycerol acetal+3PO+3EO and iso-nonyl glycerol acetal+3EO+PO—all present as mixtures of the 1,2 and 1,3 cyclic form.

Process Route A: Hydroformylation and Acetalisation of Olefins and Glycerol

In an embodiment, the invention provides a process for obtaining alkoxylated glycerol acetals encompassing the steps of:

(a1) subjecting mixtures of olefins and glycerol to combined hydroformylation and acetalisation and (a2) alkoxylating the reactions products thus obtained according to standard procedures known from the state of the art.

Olefins suitable as starting materials for joint hydroformylation and acetalisation encompass species comprising 6 to 22, preferably 8 to 12 carbon atoms and may be linear or branched. In one or more embodiments, starting materials are selected from alpha olefins, such as 1-hexene, 1-octene, 1-dodecene and the like. Typically, olefins and glycerol are reacted in a molar ratio of about 1:1 to about 5:1, preferably about 1:1.5 to about 1:3. It has been found useful to conduct the reaction in an organic solvent, preferably an aromatic non-polar solvent as for example toluene which can be easily removed by evaporation or distillation. In order to start hydroformylation it is necessary to conduct the reaction in the presence of a working amount of a transition metal hydroformylation catalyst. Such catalysts are well known from the state of the art. Rather suitable has been found a combination of $[Rh(OAc)_2]_2$ and $Ph_2P(CH_2)_2S(CH_2)_2SO_3Na$ at olefin:Rh ratios about of 500 to about 1.200, and preferably about 900 to about 1.000. The molar ratio between the transition metal complex and the phosphin ligand may vary between about 1:3 and about 1:10, preferably about 1:4 to about 1:6. Also acetalisation needs a catalyst, which is typically a strong acid like for example methane sulphonic acid or toluene sulphonic acid, employed at concentrations of about 0.1 to 0.5% b.w.—calculated on the total amounts of olefins and glycerol. Hydroformylation itself is conducted at a $CO/H_2$ (1:1) pressure of about 10 to about 100 bars and preferably about 50 bars. Typically, the joint reaction is carried out at a temperature of about 80 to about 150, preferably about 90 to about 110° C. Once the reaction is finished—typically after 5 to 48 h—the solvent is removed and the acetal obtained in yields of about 60 to 70% of theory.

Process Route B: Acetalisation of Aldehydes and Glycerol

In the alternative, a second process for obtaining alkoxylated glycerol acetals involves the following steps:

(b1) subjecting mixtures of aldehydes and glycerol to acetalisation, and (b2) alkoxylating the reaction the reactions products thus obtained according to standard procedures known from the state of the art.

Aldehydes suitable as starting materials for acetalisation encompass species comprising 6 to 22, preferably 8 to 12 carbon atoms and may be linear or branched. In one or more embodiments, starting materials are selected from aldehydes, such as n-octanal, n-decanal, n-dodecanal, benzaldehyde, furfural and the like. More preferred are branched aldehydes such as 2-ethylhexanal or iso-nonanal since these species exhibit a particular low surface tension. Typically, aldehydes and glycerol are reacted in a molar ratio of about 2:1 to about 1:2, preferably about 1:1. It has been found useful to conduct the reaction in an organic solvent, preferably an aromatic non-polar solvent as for example toluene which can be easily removed by evaporation or distillation. As explained above, acetalisation needs a catalyst, which is typically a strong acid like for example methane sulphonic acid or toluene sulphonic acid, employed at concentrations of about 0.1 to 0.5 b.w.—calculated on the total amounts of aldehydes and glycerol. Typically, the reaction is conducted under reflux at about 100 to about 120° C. over a period of about 2 to 12 h, separating off the water of condensation continuously. Once the reaction is completed, the organic solvent is evaporated and the acetals obtained in yields of about 60 to 70% of theory.

Alkoxylation

Alkoxylation of compounds with acidic hydrogen atoms is a process long known from the state of the art and well established in technical chemistry. Typically, the process is conducted in the presence of an alkaline catalyst, like for example sodium methylate or potassium tert. Butylate, preferably potassium hydroxide. Also heterogeneous catalysts like hydrotalcite are useful. Basically it is possible to use also acidic catalysts, however due to the partial degradation of the polyglycolether chain amounts of unwanted dioxane are formed. Typically, the catalysts are employed in concentrations of about 0.1 to about 1% b.w. calculated on the starting products. The alkylene oxides—ethylene oxide, propylene oxide, butylene oxide or their mixtures—are added in gaseous form to the starting products placed in the pressure reactors using a gas inlet. Typically, the reaction takes place at about 120 to about 175, preferably about 130 to about 160° C. under hydrostatic pressure of about 6 bars. The alkylene oxides can be added continuously or party-by-part. It is possible to use mixtures of different alkylene oxides—for example a mixture of ethylene oxide and propylene oxide in a molar ratio of 1:1—and add them to the starting material in order to achieve a random distribution of the different units in the chain. It is also possible to add them blockwise. Once alkoxylation is finished, the vessel is depressurised and the alkaline catalyst neutralised, usually by means of adding lactic acid.

Ethers and Esters of Alkoxylated Glycerol Acetals

As it set out in the definition for Formulas (Ia) and (Ib), the present invention also encompasses derivatives of said alkoxylated glycerol acetals which—formally spoken—represent ethers or esters of said alkoxylation products. In order to obtain said derivatives it is possible to subject the alkoxylation products to etherification or esterification. For example, an adduct of 4 moles propylene oxide and 4 moles ethylene oxide to iso-nonyl glycerol acetals can be etherified by reaction of the terminal hydroxyl group of the polyalkylene glycol chain with methyl chloride or—preferred—butyl chloride. The reaction is well known as Williamson synthesis and can be conducted by one skilled in the art without any additional inventive input. The same is true for esterification using for example short chain fatty acids like acetic acid, capronic acid, caprylic acid, caprinic acid or lauric acid.

INDUSTRIAL APPLICATION

The new alkoxylated glycerol acetals are able to reduce surface tension significantly without generating foam. Adding them to agrochemical compositions, for example comprising herbicides, insecticides, fungicides or plant growth promoters, improves the ability of the actives to stay on the surface and to penetrate into the substrates. This is a crucial benefit in order to improve efficiency of conventional biocide compositions. Improved wetting capacity and low foaming of the new products is also be of advantage in many other applications, like for example for modifying surfaces. Therefore, two additional embodiments of the present invention refer to the use of the alkoxylated glycerol acetals as additives for agrochemical compositions as well as additives for lacquers and paints.

Finally, a further embodiment of the present invention provides for agrochemical compositions, comprising
(a) biocides and
(b) alkoxylated glycerol acetals according to formulae (Ia) and (Ib).

Biocides

A biocide in the context of the present invention is a plant protection agent, more particular a chemical substance capable of killing different forms of living organisms used in fields such as medicine, agriculture, forestry, and mosquito control. In addition, plant growth regulators also belong to the group of biocides which can be divided into two sub-groups:
pesticides, which includes fungicides, herbicides, insecticides, algicides, moluscicides, miticides and rodenticides, (here, The Pesticide Manual, $14^{th}$ edition, BCPC 2006 is included as a reference, it provides information about the individual mode of actions of active ingredients) and
antimicrobials, which includes germicides, antibiotics, antibacterials, antivirals, antifungals, antiprotozoals and antiparasites.

Biocides can also be added to other materials (typically liquids) to protect the material from biological infestation and growth. For example, certain types of quaternary ammonium compounds (quats) can be added to pool water or industrial water systems to act as an algicide, protecting the water from infestation and growth of algae.

Pesticides

The U.S Environmental Protection Agency (EPA) defines a pesticide as "any substance or mixture of substances intended for preventing, destroying, repelling, or mitigating any pest". A pesticide may be a chemical substance or biological agent (such as a virus or bacteria) used against pests including insects, plant pathogens, weeds, mollusks, birds, mammals, fish, nematodes (roundworms) and microbes that compete with humans for food, destroy property, spread disease or are a nuisance. In the following examples, pesticides suitable for the agrochemical compositions according to the present invention are given:

Fungicides. A fungicide is one of three main methods of pest control—the chemical control of fungi in this case. Fungicides are chemical compounds used to prevent the spread of fungi in gardens and crops. Fungicides are also used to fight fungal infections. Fungicides can either be contact or systemic. A contact fungicide kills fungi when sprayed on its surface. A systemic fungicide has to be absorbed by the fungus before the fungus dies. Examples for suitable fungicides, according to the present invention, encompass the following chemical classes and corresponding examples:

Aminopyrimidines such as bupirimate,
Anilinopyrimidines such as cyprodinil, mepanipyrim, pyrimethanil,
Heteroaromatics such as hymexazol,
Heteroaromatic hydrocarbons such as etridiazole,
Chlorophenyls/Nitroanilines such as chloroneb, dicloran, quintozene, tecnazene, tolclofos-methyl,
Benzamide fungicides such as zoxamide,
Benzenesulfonamides such as flusulfamide,
Benzimidazoles such as acibenzolar, benomyl, benzothiazole, carbendazim, fuberidazole, metrafenone, probenazole, thiabendazole, triazoxide, and benzimidazole precursor fungicides,
Carbamates such as propamocarb, diethofencarb,
Carboxamides such as boscalid, diclocymet, ethaboxam, flutolanil, penthiopyrad, thifluzamide
Chloronitriles such chlorothalonil,
Cinnamic acid amides such as dimethomorph, flumorph,
Cyanoacetamide oximes such as cymoxanil,
Cyclopropancarboxamides such as carpropamid,
Dicarboximides such as iprodione, octhilinone, procymidone, vinclozolin
Dimethyldithiocarbamates such ferbam, metam, thiram, ziram,
Dinitroanilines such as fluazinam,
Dithiocarbamates such as mancopper, mancozeb, maneb, metiram, nabam, propineb, zineb,
Dithiolanes such as isoprothiolane,
Glucopyranosyl antibiotics such as streptomycin, validamycin,
Guanidines such as dodine, guazatine, iminoctadine,
Hexopyranosyl antibiotics such as kasugamycin,
Hydroxyanilides such as fenhexamid,
Imidazoles such as imazalil, oxpoconazole, pefurazoate, prochloraz, triflumizole,
Imidazolinones such as fenamidone,
Inorganics such as Bordeaux mixture, copper hydroxide, copper naphthenate, copper oleate, copper oxychloride, copper(II) sulfate, copper sulfate, copper(II) acetate, copper(II) carbonate, cuprous oxide, sulfur,
Isobenzofuranones such as phthalide,
Mandelamides such as mandipropamide,
Morpholines such as dodemorph, fenpropimorph, tridemorph, fenpropidin, piperalin, spiroxamine, aldimorph
Organotins such as fentin,
Oxazolidinones such as oxadixyl,
Phenylamides such as benalaxyl, benalaxyl-M, furalaxyl, metalaxyl, metalaxyl-M, ofurace,
Phenylpyrazoles such as fipronil,
Phenylpyrroles such as fludioxonil,
Phenylureas such as pencycuron,
Phosphonates such fosetyl,
Phthalamic acids such as tecloftalam,
Phthalimides such as captafol, captan, folpet,
Piperazines such as triforine,
Propionamides such as fenoxanil,
Pyridines such as pyrifenox,
Pyrimidines such as fenarimol, nuarimol,
Pyrroloquinolinones such as pyroquilon,
Qils such as cyazofamid,
Quinazolinones such as proquinazid,
Quinolines such as quinoxyfen, Quinones such as dithianon,
Sulfamides such as tolylfluanid, dichlofluanid,
Strobilurines such as azoxystrobin, dimoxystrobin, famoxadone, fluoxastrobin, kresoxim-methyl, metominostrobin, picoxystrobin, pyraclostrobin, trifloxystrobin, orysastrobin,
Thiocarbamates such as methasulfocarb,
Thiophanates such as thiophanate-methyl,
Thiophencarboxamides such silthiofam,
Triazole fungicides such as azaconazole, bitertanol, bromuconazole, cyproconazole, difenoconazole, diniconazole, epoxiconazole, fenbuconazole, fluquinconazole, flusilazole, flutriafol, fluotrimazole, hexaconazole, imibenconazole, ipconazole, metconazole, myclobutanil, penconazole, propiconazole, prothioconazole, simeconazole, tebuconazole, tetraconazole, triadimefon, triadimenol, triticonazole, quinconazole
Triazolobenzothidazoles such as tricyclazole,
Valinamide carbamates such as iprovalicarb, benthiavalicarb
Fluopicolide
Pentachlorophenol
and their mixtures.

Herbicides. An herbicide is a pesticide used to kill unwanted plants. Selective herbicides kill specific targets while leaving the desired crop relatively unharmed. Some of these act by interfering with the growth of the weed and are often based on plant hormones. Herbicides used to clear waste ground are nonselective and kill all plant material with which they come into contact. Herbicides are widely used in agriculture and in landscape turf management. They are applied in total vegetation control (TVC) programs for maintenance of highways and railroads. Smaller quantities are used in forestry, pasture systems, and management of areas set aside as wildlife habitat. In general, active ingredients representing including various chemical classes and corresponding examples can be used Anilides such as propanil
Aryloxycarboxylic acids e.g. MCPA-thioethyl
Aryloxyphenoxypropionates e.g. clodinafop-propargyl, cyhalofop-butyl, diclofops, fluazifops, haloxyfops, quizalofops,
Chloroacetamides e.g. acetolochlor, alachlor, butachlor, dimethenamid, metolachlor, propachlor
Cyclohexanedione oximes e.g. clethodim, sethoxydim, tralkoxydim,
Benzamides such as isoxaben
Benzimidazoles such as dicamba, ethofumesate
Dinitroanilines e.g. trifluralin, pendimethalin,
Diphenyl ethers e.g. aclonifen, oxyfluorfen,
The glycine derivative glyphosate, a systemic nonselective (it kills any type of plant) herbicide used in no-till burndown and for weed control in crops that are genetically modified to resist its effects,
Hydroxybenzonitriles e.g. bromoxynil,
Imidazolinones e.g. fenamidone, imazapic, imazamox, imazapic, imazapyr, imazaquin,
Isoxazolidinones e.g. clomazone
Paraquat as bypyridylium,
Phenyl carbamates e.g. desmedipham, phenmedipham,
Phenylpyrazoles e.g. pyraflufen-ethyl
Phenylpyrazolines e.g. pinoxaden,
Pyridinecarboxylic acids or synthetic auxins e.g. picloram, clopyralid, and triclopyr,
Pyrimidinyloxybenzoics e.g. bispyrtbac-sodium
Sulfonyureas e.g. amidosulfuron, azimsulfuron, bensulfuron-methyl, chlorsulfuron, flazasulfuron, foramsulfuron, flupyrsulfuron-methyl-sodium, nicosulfuron, rimsulfuron, sulfosulfuron, tribenuron-methyl, trifloxysurlfuron-sodium, triflusulfuron, tritosulfuron,
Triazolopyrimidines e.g. penoxsulam, metosulam, florasulam,
Triketones e.g. mesotriones, sulcotrione,
Ureas e.g. diuron, linuron,
Phenoxycarboxylic acids such as 2,4-D, MCPA, MCPB, mecoprops,
Triazines such as atrazine, simazine, terbuthylazine,
and their mixtures.

Insecticides. An insecticide is a pesticide used against insects in all developmental forms. They include ovicides and larvicides used against the eggs and larvae of insects. Insecticides are used in agriculture, medicine, industry and the household. In the following, suitable chemical classes and examples of insecticides are mentioned:

Abamectin, emamectin,
Anthranilic diamides such as rynaxypyr
Synthetic auxins Duch as avermectin,
Amidines such as amitraz,
Anthranilic diamide Duch as rynaxypyr,
Carbamates such as aldicarb, carbofuran, carbaryl, methomyl, 2-(1-methylpropyl)phenyl methylcarbamate,
Chlorinated insecticides such as, for example, Camphechlor, DDT, Hexachlorocyclohexane, gamma-Hexachlorocyclohexane, Methoxychlor, Pentachlorophenol, TDE, Aldrin, Chlordane, Chlordecone, Dieldrin, Endosulfan, Endrin, Heptachlor, Mirex,
Juvenile hormone mimics such as pyriproxyfen,
Neonicotinoids such as imidacloprid, clothianidin, thiacloprid, thiamethoxam,
Organophosphorus compounds such as acephate, azinphos-methyl, bensulide, chlorethoxyfos, chlorpyrifos, chlorpyriphos-methyl, diazinon, dichlorvos (DDVP), dicrotophos, dimethoate, disulfoton, dthoprop, fenamiphos, fenitrothion, fenthion, fosthiazate, malathion, methamidophos, methidathion, methyl-parathion, mevinphos, naled, omethoate, oxydemeton-methyl, parathion, phorate, phosalone, phosmet, phostebupirim, pirimiphos-methyl, profenofos, terbufos, tetrachlorvinphos, tribufos, trichlorfon,
Oxadiazines such as indoxacarb,
Plant toxin derived compounds such as derris (rotenone), pyrethrum, neem (azadirachtin), nicotine, caffeine,
Pheromones such cuellure, methyl eugenol,
Pyrethroids such as, for example, allethrin, bifenthrin, deltamethrin, permethrin, resmethrin, sumithrin, tetramethrin, tralomethrin, transfluthrin,
Selective feeding blockers such as flonicamid, pymetrozine,
Spinosyns e.g. spinosad
and their mixtures.

Plant Growth Regulators. Plant hormones (also known as phytohormones) are chemicals that regulate plant growth. Plant hormones are signal molecules produced within the plant, and occur in extremely low concentrations. Hormones regulate cellular processes in targeted cells locally and when moved to other locations, in other locations of the plant. Plants, unlike animals, lack glands that produce and secrete hormones. Plant hormones shape the plant, affecting seed growth, time of flowering, the sex of flowers, senescence of leaves and fruits. They affect which tissues grow upward and which grow downward, leaf formation and stem growth, fruit development and ripening, plant longevity and even plant death. Hormones are vital to plant growth and lacking them, plants would be mostly a mass of undifferentiated cells. In the following, suitable plant growth regulators are mentioned:

Aviglycine,
Cyanamide,
Gibberellins such gibberellic acid,
Quaternary ammoniums such as chlormequat chloride, mepiquat chloride,
Ethylene generators such ethephone, Rodenticides. Rodenticides are a category of pest control chemicals intended to kill rodents. Rodents are difficult to kill with poisons because their feeding habits reflect their place as scavengers. They would eat a small bit of something and wait, and if they do not get sick, they would continue eating. An effective rodenticide must be tasteless and odorless in lethal concentrations, and have a delayed effect. In the following, examples for suitable rodenticides are given:

Anticoagulants are defined as chronic (death occurs after 1-2 weeks post ingestion of the lethal dose, rarely sooner), single-dose (second generation) or multiple dose (first generation) cumulative rodenticides. Fatal internal bleeding is caused by lethal dose of anticoagulants such as brodifacoum, coumatetralyl or warfarin. These substances in effective doses are antivitamins K, blocking the enzymes $K_1$-2,3-epoxide-reductase (this enzyme is preferentially blocked by 4-hydroxycoumarin/4-hydroxythiacoumarin derivatives) and $K_1$-quinone-reductase (this enzyme is preferentially blocked by indandione derivatives), depriving the organism of its source of active vitamin $K_1$. This leads to a disruption of the vitamin K cycle, resulting in an inability of production of essential blood-clotting factors (mainly coagulation factors II (prothrombin), VII (proconvertin), IX (Christmas factor) and X (Stuart factor)). In addition to this specific metabolic disruption, toxic doses of 4-hydroxycoumarin/4-hydroxythiacoumarin and indandione anticoagulants are causing damage to tiny blood vessels (capillaries), increasing their permeability, causing diffuse internal bleedings (haemorrhagias). These effects are gradual; they develop in the course of days and are not accompanied by any nociceptive perceptions, such as pain or agony. In the final phase of intoxication the exhausted rodent collapses in hypovolemic circulatory shock or severe anemia and dies calmly. Rodenticidal anticoagulants are either first generation agents (4-hydroxycoumarin type: warfarin, coumatetralyl; indandione type: pindone, diphacinone, chlorophacinone), generally requiring higher concentrations (usually between 0.005 and 0.1%), consecutive intake over days in order to accumulate the lethal dose, poor active or inactive after single feeding and less toxic than second generation agents, which are derivatives of 4-hydroxycoumarin (difenacoum, brodifacoum, bromadiolone and flocoumafen) or 4-hydroxy-1-benzothiin-2-one (4-hydroxy-1-thiacournarin, sometimes incorrectlly referred to as 4-hydroxy-1-thiocotunarin, for reason see heterocyclic compounds), namely difethialone. Second generation agents are far more toxic than first generation agents, they are generally applied in lower concentrations in baits (usually in the order of 0.001-0.005%), and are lethal after single ingestion of bait and are effective also against strains of rodents that have become resistant against first generation anticoagulants; thus the second generation anticoagulants are sometimes referred to as "superwarfarins". Sometimes, anticoagulant rodenticides are potentiated by an antibiotic, most commonly by sulfaquinoxaline. The aim of this association (e.g. warfarin 0.05%+sulfaquinoxaline 0.02%, or difenacoum 0.005%+sulfaquinoxaline 0.02% etc.) is that the antibiotic/bacteriostatic agent suppresses intestinal/gut symbiotic microflora that represents a source of vitamin K. Thus the symbiotic bacteria are killed or their metabolism is impaired and the production of vitamin K by them is diminuted, an effect which logically contributes to the action of anticoagulants. Antibiotic agents other than sulfaquinoxaline may be used, for example co-trimoxazole, tetracycline, neomycin or metronidazole. A further synergism used in rodenticidal baits is that of an association of an anticoagulant with a compound with vitamin D-activity, i.e. cholecalciferol or ergocalciferol (see below). A typical formula used is, e.g., warfarin 0.025-0.05%+cholecalciferol 0.01%. In some countries there are even fixed three-component rodenticides, i.e. anticoagulant+antibiotic+vitamin D, e.g. difenacoum 0.005%+sulfaquinoxaline 0.02%+cholecalciferol 0.01%. Associations of a second-generation anticoagulant with an antibiotic and/or vitamin D are considered to be effective even against the most resistant strains of rodents, though some second generation anticoagulants (namely brodifacoum and difethialone), in bait concentrations of 0.0025-0.005% are so toxic that no known resistant strain of rodents exists and even rodents resistant against any other derivatives are reliably exterminated by application of these most toxic anticoagulants.

Vitamin $K_1$ has been suggested and successfully used as an antidote for pets or humans, which/who were either accidentally or intentionally (poison assaults on pets, suicidal attempts) exposed to anticoagulant poisons. In addition, since some of these poisons act by inhibiting liver functions and in progressed stages of poisoning, several blood-clotting factors as well as the whole volume of circulating blood lacks, a blood transfusion (optionally with the clotting factors present) can save a person's life who inadvertently takes them, which is an advantage over some older poisons.

Metal phosphides have been used as a means of killing rodents and are considered single-dose fast acting rodenticides (death occurs commonly within 1-3 days after single bait ingestion). A bait consisting of food and a phosphide (usually zinc phosphide) is left where the rodents can eat it. The acid in the digestive system of the rodent reacts with the phosphide to generate the toxic phosphine gas. This method of vermin control has possible use in places where rodents are resistant to some of the anticoagulants, particularly for control of house and field mice; zinc phosphide baits are also cheaper than most second-generation anticoagulants, so that sometimes, in cases of large infestation by rodents, their population is initially reduced by copious amounts of zinc phosphide bait applied, and the rest of the population that survived the initial fast-acting poison is then eradicated by prolonged feeding on anticoagulant bait. Inversely, the individual rodents that survived anticoagulant bait poisoning (rest population) can be eradicated by pre-baiting them with nontoxic bait for a week or two (this is important to overcome bait shyness, and to get rodents used to feeding in specific areas by offering specific food, especially when eradicating rats) and subsequently applying poisoned bait of the same sort as used for pre-baiting until all consumption of the bait ceases (usually within 2-4 days). These methods of alternating rodenticides with different modes of action provides a factual or an almost 100% eradication of the rodent population in the area if the acceptance/palatability of bait is good (i.e., rodents readily feed on it).

Phosphides are rather fast acting rat poisons, resulting in that the rats are dying usually in open areas instead of the affected buildings. Typical examples are aluminum phosphide (fumigant only), calcium phosphide (fumigant only), magnesium phosphide (fumigant only) and zinc phosphide (in baits). Zinc phosphide is typically added to rodent baits in amounts of around 0.75-2%. The baits have a strong, pungent garlic-like odor characteristic for phosphine liberated by hydrolysis. The odor attracts (or, at least, does not repulse) rodents, but has a repulsive effect on other mammals; birds, however (notably wild turkeys), are not sensitive to the smell and feed on the bait thus becoming collateral damage.

Hypercalcemia. Calciferols (vitamins D), cholecalciferol (vitamin $D_3$) and ergocalciferol (vitamin $D_2$) are used as rodenticides, which are toxic to rodents for the same reason that they are beneficial to mammals: they are affecting calcium and phosphate homeostasis in the body. Vitamins D are essential in minute quantities (few IUs per kilogram body weight daily, which is only a fraction of a milligram), and like most fat soluble vitamins they are toxic in larger doses as they readily result in the so-called hypervitaminosis, which is, simply said, poisoning by the vitamin. If the poisoning is severe enough (that is, if the dose of the toxicant is high enough), it eventually leads to death. In rodents consuming the rodenticidal bait it causes hypercalcemia by raising the calcium level, mainly by increasing calcium absorption from food, mobilising bone-matrix-fixed calcium into ionised form (mainly monohydrogencarbonate calcium cation, partially bound to plasma proteins, $[CaHCO_3]^+$), which circulates dissolved in the blood plasma, and after ingestion of a lethal dose the free calcium levels are raised sufficiently so that blood vessels, kidneys, the stomach wall and lungs are mineralised/calcificated (formation of calcificates, crystals of calcium salts/complexes in the tissues thus damaging them), leading further to heart problems (myocard is sensitive to variations of free calcium levels that are affecting both myocardial contractility and excitation propagation between atrias and ventriculas) and bleeding (due to capillary damage) and possibly kidney failure. It is considered to be single-dose, or cumulative (depending on concentration used; the common 0.075% bait concentration is lethal to most rodents after a single intake of larger portions of the bait), sub-chronic (death occurring usually within days to one week after ingestion of the bait). Applied concentrations are 0.075% cholecalciferol and 0.1% ergocalciferol when used alone. There is an important feature of calciferols toxicology which is that they are synergistic with anticoagulant toxicants. This means that mixtures of anticoagulants and calciferols in the same bait are more toxic than the sum of toxicities of the anticoagulant and the calciferol in the bait so that a massive hypercalcemic effect can be achieved by substantially lower calciferol content in the bait and vice-versa. More pronounced anticoagulant/hemorrhagic effects are observed if calciferol is present. This synergism is mostly used in baits low in calciferol because effective concentrations of calciferols are more expensive than effective concentrations of most anticoagulants. The historically very first application of a calciferol in rodenticidal bait was, in fact, the Sorex product Sorexa® D (with a different formula than today's Sorexa® D) back in the early 1970's, containing warfarin 0.025%+ergocalciferol 0.1%. Today, Sorexa® CD contains a 0.0025% difenacoum+0.075% cholecalciferol combination. Numerous other brand products containing either calciferols 0.075-0.1% (e.g. Quintox®, containing 0.075% cholecalciferol) alone, or a combination of calciferol 0.01-0.075% with an anticoagulant are marketed.

Miticides, moluscicides and nematicides. Miticides are pesticides that kill mites. Antibiotic miticides, carbamate miticides, formamidine miticides, mite growth regulators, organochlorine, permethrin and organophosphate miticides all belong to this category. Molluscicides are pesticides used to control mollusks, such as moths, slugs and snails. These substances include metaldehyde, methiocarb and aluminium sulfate. A nematicide is a type of chemical pesticide used to kill parasitic nematodes (a phylum of worm). A nematicide is obtained from a neem tree's seed cake; which is the residue of neem seeds after oil extraction. The neem tree is known by several names in the world but was first cultivated in India since ancient times.

Antimicrobials

In the following examples, antimicrobials suitable for agrochemical compositions according to the present invention are given. Bactericidal disinfectants mostly used are those applying active chlorine (i.e., hypochlorites, chloramines, dichloroisocyanurate and trichloroisocyanurate, wet chlorine, chlorine dioxide, etc.), active oxygen (peroxides such as peracetic acid, potassium persulfate, sodium perborate, sodium percarbonate and urea perhydrate), iodine (iodpovidone (povidone-iodine, Betadine), Lugol's solution, iodine tincture, iodinated nonionic surfactants), concentrated alcohols (mainly ethanol, 1-propanol, called also n-propanol and 2-propanol, called isopropanol and mixtures thereof; further, 2-phenoxyethanol and 1- and and 2-phenoxypropanols are used), phenolic substances (such as phenol (also called "carbolic acid"), cresols (called "Lysole" in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants such as some quaternary ammonium cations (such as benzalkonium chloride, cetyl trimethylammonium bromide or chloride, didecyldimethylammonium chloride, cetylpyridinium chloride, benzethonium chloride) and others, non-quarternary compounds such as chlorhexidine, glucoprotamine, octenidine dihydrochloride, etc.), strong oxidizers such as ozone and permanganate solutions;

heavy metals and their salts such as colloidal silver, silver nitrate, mercury chloride, phenylmercury salts, copper sulfate, copper oxide-chloride etc. Heavy metals and their salts are the most toxic and environmentally hazardous bactericides and, therefore, their use is strongly suppressed or forbidden; further, also properly concentrated strong acids (phosphoric, nitric, sulfuric, amidosulfuric, toluenesulfonic acids) and alcalis (sodium, potassium, calcium hydroxides) between pH<1 or >13, particularly below elevated temperatures (above 60° C.) kill bacteria.

As antiseptics (i.e., germicide agents that can be used on human or animal body, skin, mucoses, wounds and the like), few of the above mentioned disinfectants can be used under proper conditions (mainly concentration, pH, temperature and toxicity toward man/animal). Among them, important are

- Some properly diluted chlorine preparations (e.g. Daquin's solution, 0.5% sodium or potassium hypochlorite solution, pH-adjusted to pH 7-8, or 0.5-1% solution of sodium benzenesulfochloramide (chloramine B)), some iodine preparations such as iodopovidone in various galenics (ointments, solutions, wound plasters), in the past also Lugol's solution,
- peroxides as urea perhydrate solutions and pH-buffered 0.1-0.25% peracetic acid solutions,
- alcohols with or without antiseptic additives, used mainly for skin antisepsis,
- weak organic acids such as sorbic acid, benzoic acid, lactic acid and salicylic acid
- some phenolic compounds such as hexachlorophene, triclosan and Dibromol, and
- cation-active compounds such as 0.05-0.5% benzalkonium, 0.5-4% chlorhexidine, 0.1-2% octenidine solutions.

Bactericidal antibiotics kill bacteria; bacteriostatic antibiotics only slow down their growth or reproduction. Penicillin is a bactericide, as are cephalosporins. Aminoglycosidic antibiotics can act in both a bactericidic manner (by disrupting cell wall precursor leading to lysis) or bacteriostatic manner (by connecting to 30s ribosomal subunit and reducing translation fidelity leading to inaccurate protein synthesis). Other bactericidal antibiotics according to the present invention include the fluoroquinolones, nitrofurans, vancomycin, monobactams, co-trimoxazole, and metronidazole Preferred actives are those with systemic or partially systemic mode of action such as for example azoxystrobin.

EXAMPLES

Synthesis Route A

Hydroformylation of alpha olefins and in-situ reaction with glycerol

Manufacturing Example M1

Hydroformylation and acetalisation of 1-octene and glycerol 16.0 ml 1-octene (100 mmol), 10 ml toluene, 4 ml glycerol (5 g, 5.5 mmol), 30 mg p-toluenesulfonic acid, 1.55 mg [Rh(COD)acac] (0.005 mmol) and 6.55 mg (0.025 mmol) Ph3P in 0.5 ml toluene (Olefin:Rh ratio=10 000) were charged in a 100 ml lab autoclave (Parr Instruments) equipped with a gas entrainment stirrer. Hydroformylation and acetalisation was performed at 50 bars CO/H2=1/1 at 100° C. for 5 hrs. The yield was 58% with 69% acetal purity (GC Area).

Manufacturing Example M2

Hydroformylation and acetalisation of 1-dodecene and glycerol 20.0 ml 1-dodecene (90 mmol), 5 ml water, 2 ml glycerol (2.5 g, 2.75 mmol), 50 mg p-toluenesulfonic acid, 22 mg [Rh(OAc)2]2 (0.05 mmol) and 188 mg (0.50 mmol) Ph2P (CH2)2S(CH2)2SO3Na (Olefin:Rh ratio=900) were charged in a 100 ml lab autoclave (Parr Instruments) equipped with a gas entrainment stirrer. Hydroformylation and acetalisation was performed at 50 bars CO/H2=1/1 at 120° C. for 24 hrs. The yield was 99% with 69% acetal purity (GC Area).

Synthesis Route B

Direct reaction of aldehydes with glycerol

Manufacturing Example M3

Synthesis of glycerol acetals with dodecanal 1472 g (8 Mol) dodecanal, 773 g (8.4 Mol) glycerol, 1200 ml toluene and 2 g p-toluenesulfonic acid were stirred for 2.5 hrs under reflux and water removal. 155 ml of water was produced. Toluene was removed by evaporation in a rotary evaporator at 50° C. The product was distilled; the yield was 2174 g (78%).

Manufacturing Example M4

Synthesis of glycerol acetals with decanal 688 g decanal (4.4 Mol), 421 g glycerol (4.6 Mol), 1000 ml toluene and 1.1 g p-toluenesulfonic acid were stirred at 110° C. for 5 hrs under reflux and water removal. 65 ml of water was produced. The product was neutralized with sodium hydroxide to pH 7.0 and washed with water. Toluene was removed by evaporation in a rotary evaporator at 50° C. The product was obtained with 94% acetal purity (GC Area).

Manufacturing Example M5

Synthesis of glycerol acetals with isononanal 629 g isononanal (4.4 Mol), 421 g glycerol (4.6 Mol), 1000 ml toluene and 1.1 g p-toluenesulfonic acid were stirred at 110° C. for 5 hrs under reflux and water removal. 70 ml of water was produced. The product was neutralized with sodium hydroxide to pH 7.0 and washed with water. Toluene was removed by evaporation in a rotary evaporator at 50° C. The product was obtained with 93% acetal purity (GC Area).

Manufacturing Example M6

Synthesis of glycerol acetals with octanal in pilot scale 16.6 kg (130 Mol) octanal, 12.6 kg (137 Mol) glycerol, 40 l toluene and 33 g p-toluenesulfonic acid were stirred and heated to 110° C. for 5 hrs. Water was removed by distillation of water/toluene azeotrope. When no further water is produced, the reaction mixture was cooled to 80° C., neutralized by addition of sodium hydroxide to pH 7.0 and washed with water. The toluene was removed by evaporation and the product is dried by vacuum. 23.5 kg of acetal with 95% purity (GC Area) was obtained.

Manufacturing Example M7

Synthesis of n-octyl glycerol acetal+4PO+4EO 1.920 g (10 Mol) n-octyl glycerol acetal obtained from Example M7 was placed in a 10-l-stirred autoclave and 30 g of sodium methylate (30% b.w. solution in methanol) added. The reactor was purged with nitrogen and heated to 155° C. Subsequently, 2.640 g (40 Mol) propylene oxide was added and reacted until the pressure started to decrease. Then 1.760 g (40 Mol) ethylene oxide was added. After a reaction time of 4 h the reactor was cooled to room temperature, depressurised and neutralised by adding an aqueous solution of lactic acid. The alkoxylation product was obtained as a clear liquid of light yellow colour.

Application Examples 1 to 13, Comparative Examples C1 to C4

Performance Tests with Selected Products

Foam properties and surface tension of various alkoxylated glycerol acetals were compared with data obtained from conventional fatty alcohol alkoxylates at 0.1 and 0.25% b.w. concentration, respectively. Foam potential was tested with SITA foam tester R-2000, available from SITA Messtechnik GmbH, Gostritzer Str. 61-63, 01217 Dresden, Germany. Dynamic surface tension was determined with the tensiometer SITA science line t60, ibid.

The data are presented in the following tables 1a and 1b. "R" denotes the type of the alkyl residue linked to the cyclic acetal body; "AO" explains type and number of ethylene and/or propylene oxide units attached to the free hydroxyl group of the acetals. Column 3 explains according to which synthesis route—starting either from the olefins or the aldehydes—the acetals were obtained. Examples 1 to 13 illustrate the invention; examples C1 to C4 are presented for the purpose of comparison.

TABLE 1a

Structure and Properties at 0.1% aqueous solution/dispersion

| Example | R | AO | Synthesis route | Foam [ml] after 1 min/5 min | Surface Tension [mN/m] at 10 Hz | Surface Tension [mN/m] at 0.1 Hz |
|---|---|---|---|---|---|---|
| 1 | R = n-$C_8$ | AO = 4PO + 4EO | B | 30  25 | 44 | 32 |
| 2 | R = n-$C_{10}$ | AO = 4PO + 4EO | A | 100  80 | 52 | 30 |
| 3 | R = n-$C_{10}$ | AO = 4PO + 4EO | B | 120  110 | 50 | 31 |
| 4 | R = iso-$C_9$ | AO = 3EO + 3PO | A | 0  0 | 45 | 36 |
| 5 | R = iso-$C_9$ | AO = 3PO + 3EO | A | 0  0 | 43 | 31 |
| C1 | Isodecanol + 6EO | | — | 225  210 | 40 | 27 |
| C2 | Decanol + 5EO | | — | 190  170 | 40 | 26 |

TABLE 1b

Structure and Properties at 0.25% aqueous solution/dispersion

| Example | R | AO | Synthesis route | Surface Tension [mN/m] at 10 Hz | Surface Tension [mN/m] at 0.1 Hz |
|---|---|---|---|---|---|
| 6 | R = n-$C_8$ | AO = 10EO | B | 45 | 36 |
| 7 | R = n-$C_{10}$ | AO = 10EO | A | 40 | 32 |
| 8 | R = n-$C_{12}$ | AO = 10EO | A | 66 | 33 |
| 9 | R = n-$C_8$ | AO = 4PO + 4EO | B | 39 | 32 |
| 10 | R = n-$C_{10}$ | AO = 4PO + 4EO | A | 38 | 32 |
| 11 | R = n-$C_{10}$ | AO = 4PO + 4EO | B | 44 | 31 |
| 12 | R = iso-$C_9$ | AO = 3EO + 3PO | A | 37 | 29 |
| 13 | R = iso-$C_9$ | AO = 3PO + 3EO | A | 36 | 29 |
| C3 | Isodecanol + 6EO | | — | 34 | 27 |
| C4 | Decanol + 5EO | | — | 33 | 26 |

What is claimed is:

1. A method of preparing agrochemical compositions comprising adding as an additive to the agrochemical compositions comprising a biocide, alkoxylated glycerol acetal according to Formulas (Ia) and (Ib):

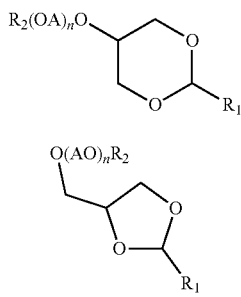

wherein:
- $R_1$ comprises a linear or branched alkyl radical having 8 to 12 carbon atoms,
- $R_2$ is selected from hydrogen, an alkyl, alkenyl or hydroxyalkyl group having 2 to 22 carbon atoms or an acyl group having 2 to 22 carbon atoms and 0 or 1 to 3 double bonds, and AO represents a mixture of ethylene oxide (EO) and propylene oxide (PO) units, and n is an integer of 4 to 8.

2. An agrochemical composition comprising:
(a) a biocide, and
(b) an alkoxylated glycerol acetal according to Formulas (Ia) and (Ib):

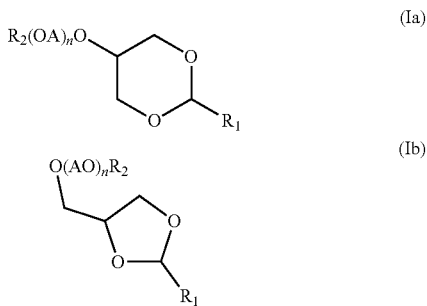

wherein:
- $R_1$ comprises a linear or branched alkyl radical having 8 to 12 carbon atoms,
- $R_2$ is selected from hydrogen, an alkyl, alkenyl or hydroxyalkyl group having 2 to 22 carbon atoms or an acyl group having 2 to 22 carbon atoms and 0 or 1 to 3 double bonds, and AO represents a mixture of ethylene oxide (EO) and propylene oxide (PO) units, and n is an integer of 4 to 8.

3. The agrochemical composition of claim 2, wherein the alkoxylated glycerol acetal comprises n-octyl glycerol acetal 4PO, and 4EO.

4. The agrochemical composition of claim 2, wherein the alkoxylated glycerol acetal comprises n-decyl glycerol acetal, 4PO, and 4EO.

5. The agrochemical composition of claim 2, wherein $R_2$ of the alkoxylated glycerol acetal is selected from hydrogen, an alkyl radical having 4 to 8 carbon atoms, or an acyl radical having 4 to 8 carbon atoms.

6. The agrochemical composition of claim 2, wherein AO of the alkoxylated glycerol acetal comprises mixtures of ethylene and propylene units, either randomised or blockwise.

* * * * *